(12) United States Patent
WasDyke

(10) Patent No.: US 7,896,898 B2
(45) Date of Patent: Mar. 1, 2011

(54) SELF-CENTERING BLOOD CLOT FILTER

(75) Inventor: Joel M. WasDyke, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1239 days.

(21) Appl. No.: 10/630,307

(22) Filed: Jul. 30, 2003

(65) Prior Publication Data
US 2005/0027314 A1 Feb. 3, 2005

(51) Int. Cl.
*A61F 2/06* (2006.01)
*A61M 29/00* (2006.01)

(52) U.S. Cl. ......... 606/200; 606/191; 606/198; 623/1.15

(58) Field of Classification Search ............... 606/200, 606/191, 194, 195, 198; 623/1.11, 1.15
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 3,952,747 A | 4/1976 | Kimmell, Jr. | |
| 4,425,908 A * | 1/1984 | Simon ........................... | 128/899 |
| 4,494,531 A | 1/1985 | Gianturco | |
| 4,688,553 A | 8/1987 | Metals | |
| 4,957,501 A | 9/1990 | Lahille et al. | |
| 4,969,891 A | 11/1990 | Gewertz | |
| 5,108,418 A * | 4/1992 | Lefebvre ....................... | 606/200 |
| 5,133,733 A | 7/1992 | Rasmussen et al. | |
| 5,152,777 A | 10/1992 | Goldberg et al. | |
| 5,160,342 A | 11/1992 | Reger et al. | |
| 5,370,657 A | 12/1994 | Irie | |
| 5,626,605 A | 5/1997 | Irie et al. | |
| 5,695,519 A | 12/1997 | Summers et al. | |
| 5,709,704 A | 1/1998 | Nott et al. | |
| 5,776,162 A * | 7/1998 | Kleshinski ................... | 623/1.18 |
| 5,814,064 A | 9/1998 | Daniel et al. | |
| 5,827,324 A | 10/1998 | Cassell et al. | |
| 5,836,968 A | 11/1998 | Simon et al. | |
| 5,925,016 A | 7/1999 | Chornenky et al. | |
| 5,935,139 A | 8/1999 | Bates | |
| 5,941,896 A | 8/1999 | Kerr | |

(Continued)

FOREIGN PATENT DOCUMENTS

WO   WO 01/58381 A   8/2001

*Primary Examiner* — Vy Q Bui
(74) *Attorney, Agent, or Firm* — Seager, Tufte & Wickhem LLC

(57) ABSTRACT

Blood clot filters having self-centering capabilities when placed in a blood vessel are disclosed. A blood clot device in accordance with an exemplary embodiment of the present invention may include a number filter legs formed at least in part of a shape-memory material configured to transform from a centering configuration to a filtering when deployed in the body. An attachment section on the distal section of each filter leg is configured to pierce and secure the filter to the vessel wall at a first location. A bend region may be heat set into the shape-memory material to provide a second contact location along the vessel wall to aid in centering the filter within the vessel. The bend region can be formed by heating the shape-memory material above its final austenite temperature ($A_f$), and then shaping the filter leg to form a pad that abuts the vessel wall during deployment.

14 Claims, 3 Drawing Sheets

U.S. PATENT DOCUMENTS

| | | |
|---|---|---|
| 6,001,118 A | 12/1999 | Daniel et al. |
| 6,007,558 A | 12/1999 | Ravenscroft et al. |
| 6,053,932 A | 4/2000 | Daniel et al. |
| 6,059,814 A | 5/2000 | Ladd |
| 6,066,149 A | 5/2000 | Samson et al. |
| 6,068,645 A | 5/2000 | Tu |
| 6,152,946 A | 11/2000 | Broome et al. |
| 6,165,200 A | 12/2000 | Tsugita et al. |
| 6,171,327 B1 | 1/2001 | Daniel et al. |
| 6,179,859 B1 | 1/2001 | Bates et al. |
| 6,203,561 B1 | 3/2001 | Ramee et al. |
| 6,214,025 B1 | 4/2001 | Thistle et al. |
| 6,231,589 B1 | 5/2001 | Wessman et al. |
| 6,331,183 B1 | 12/2001 | Suon |
| 6,346,116 B1 | 2/2002 | Brooks et al. |
| 6,428,559 B1 | 8/2002 | Johnson |
| 6,432,122 B1 | 8/2002 | Gilson et al. |
| 6,443,972 B1 | 9/2002 | Bosma et al. |
| 6,482,222 B1 | 11/2002 | Bruckheimer et al. |
| 6,485,502 B2 | 11/2002 | Don Michael et al. |
| 6,506,205 B2 | 1/2003 | Goldberg et al. |
| 6,511,496 B1 | 1/2003 | Huter et al. |
| 6,511,497 B1 | 1/2003 | Braun et al. |
| 6,540,722 B1 | 4/2003 | Boyle et al. |
| 6,544,276 B1 | 4/2003 | Azizi |
| 6,544,280 B1 | 4/2003 | Daniel et al. |
| 6,551,342 B1 | 4/2003 | Shen et al. |
| 6,558,405 B1 | 5/2003 | McInnes |
| 6,569,183 B1 | 5/2003 | Kim et al. |
| 6,572,605 B1 | 6/2003 | Humes |
| 6,575,996 B1 | 6/2003 | Denison et al. |
| 6,589,266 B2 | 7/2003 | Whitcher et al. |
| 6,602,272 B2 * | 8/2003 | Boylan et al. ............ 606/200 |
| 6,949,103 B2 * | 9/2005 | Mazzocchi et al. ........ 606/108 |
| 2002/0022860 A1 | 2/2002 | Borillo et al. |
| 2002/0062135 A1 | 5/2002 | Mazzocchi et al. |
| 2003/0078519 A1 | 4/2003 | Salahieh et al. |

* cited by examiner

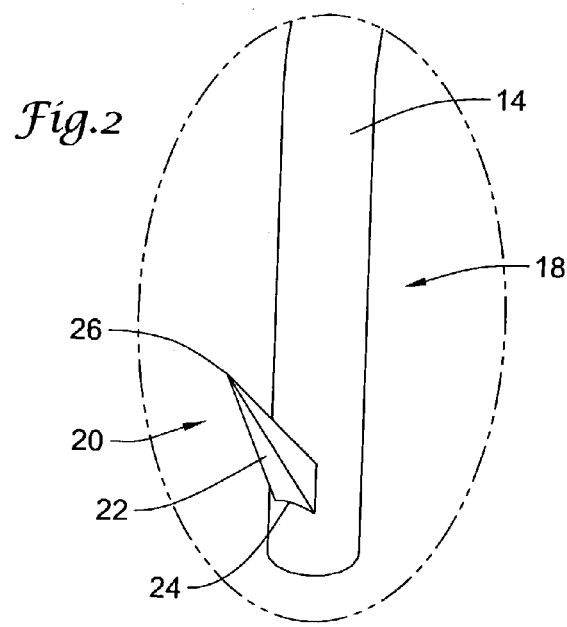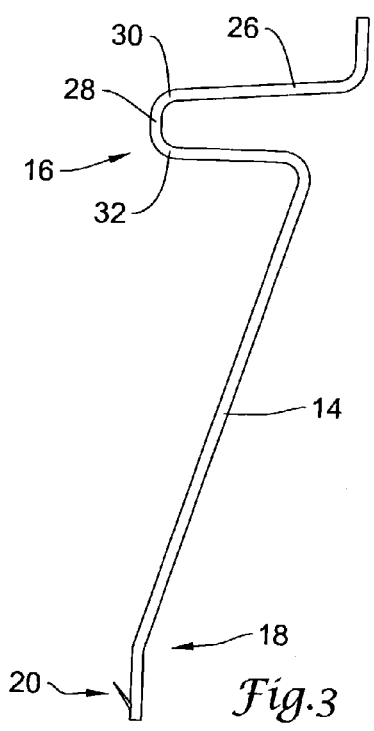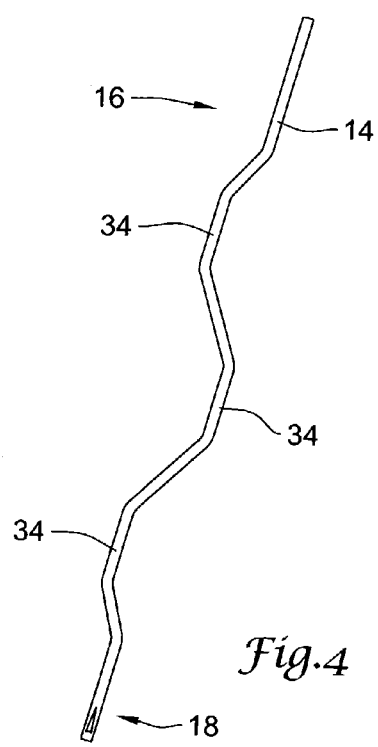

SELF-CENTERING BLOOD CLOT FILTER

FIELD OF THE INVENTION

The present invention relates to devices for filtering blood clots within the body. More specifically, the present invention pertains to blood clot filters having self-centering capabilities within a blood vessel.

BACKGROUND OF THE INVENTION

Blood clot filters are typically used in combination with other thrombolytic agents to treat pulmonary embolism occurring within a patient. These devices are generally implanted within a vessel such as the inferior vena cava, and function by capturing blood clots (emboli) contained in the blood stream before they can reach the lungs and cause permanent damage to the body. To trap emboli contained within the blood, many conventional blood clot filters utilize a plurality of independent filter legs coupled to an apical head that can be expanded within the body to form a conical-shaped surface that captures blood clots without disturbing the flow of blood. Once collected, a natural clot lysing process occurs within the body to dissolve the blood clots collected by the filter.

Delivery of the blood clot filter within the body is generally accomplished via an introducer sheath percutaneously inserted through the femoral (groin) or jugular (neck) veins. Such introducer sheaths are generally tubular in shape, and include an inner lumen configured to transport the filter in a collapsed position through the body. Once transported to a desired location in the body, the filter can then be removed from within the introducer sheath, allowing the filter legs to spring open and engage the vessel wall. A needle, hook, barb, prong, wedge or other attachment means disposed on the base of each filter leg can be used to secure the filter to the vessel wall.

The efficacy of the blood clot filter to capture blood clots is dependent in part on the ability of the filter to center when deployed from within the introducer sheath. Tilting of the filter may result if the apical head is not aligned centrally within the vessel, causing the filter legs to asymmetrically engage the vessel wall. In certain circumstances, tilting of the filter may affect the ability of the device to capture blood clots contained in the blood. To overcome this problem, more recent designs in the art have focused on blood clot filters having the ability to self-center when placed in the body. These designs, while providing a means to center the filter within the vessel, typically add to the complexity and size of the filter and accompanying introducer sheath.

SUMMARY OF THE INVENTION

The present invention pertains to blood clot filters having self-centering capabilities when placed in a blood vessel. A blood clot filter in accordance with an exemplary embodiment of the present invention includes several radially expandable filter legs formed at least in part of a shape-memory material configured to transform from a centering configuration to a filtering configuration within the body. Each filter leg may be coupled proximally to an apical head that forms a common apex of the filter. The distal section of each filter leg may include a needle, hook, barb, prong, wedge or other suitable attachment means for securing the filter to the wall of the blood vessel.

The blood clot filter can be configured to assume a centering configuration automatically upon deployment within the vessel. In certain embodiments, for example, a bend region on each filter leg can be formed by heating the shape memory material above its final austenite temperature ($A_f$), and then shaping the filter leg to form a pad which abuts the vessel wall to center the filter within the blood vessel. The shape-memory material can be configured to transform from martensite to austenite at a particular temperature or temperature range at, above, or below body temperature, causing the filter leg to assume a filtering shape configured to capture blood clots.

BRIEF DESCRIPTION OF THE DRAWINGS

FIG. 2 is an enlarged perspective view of the distal section of one of the filter legs illustrated in FIG. 1;

FIG. 3 is a side perspective view of one of the filter legs illustrated in FIG. 1, showing the filter leg in the centering configuration;

FIG. 4 is another side perspective view of the filter leg illustrated in FIG. 3, showing the filter leg in the filtering configuration;

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
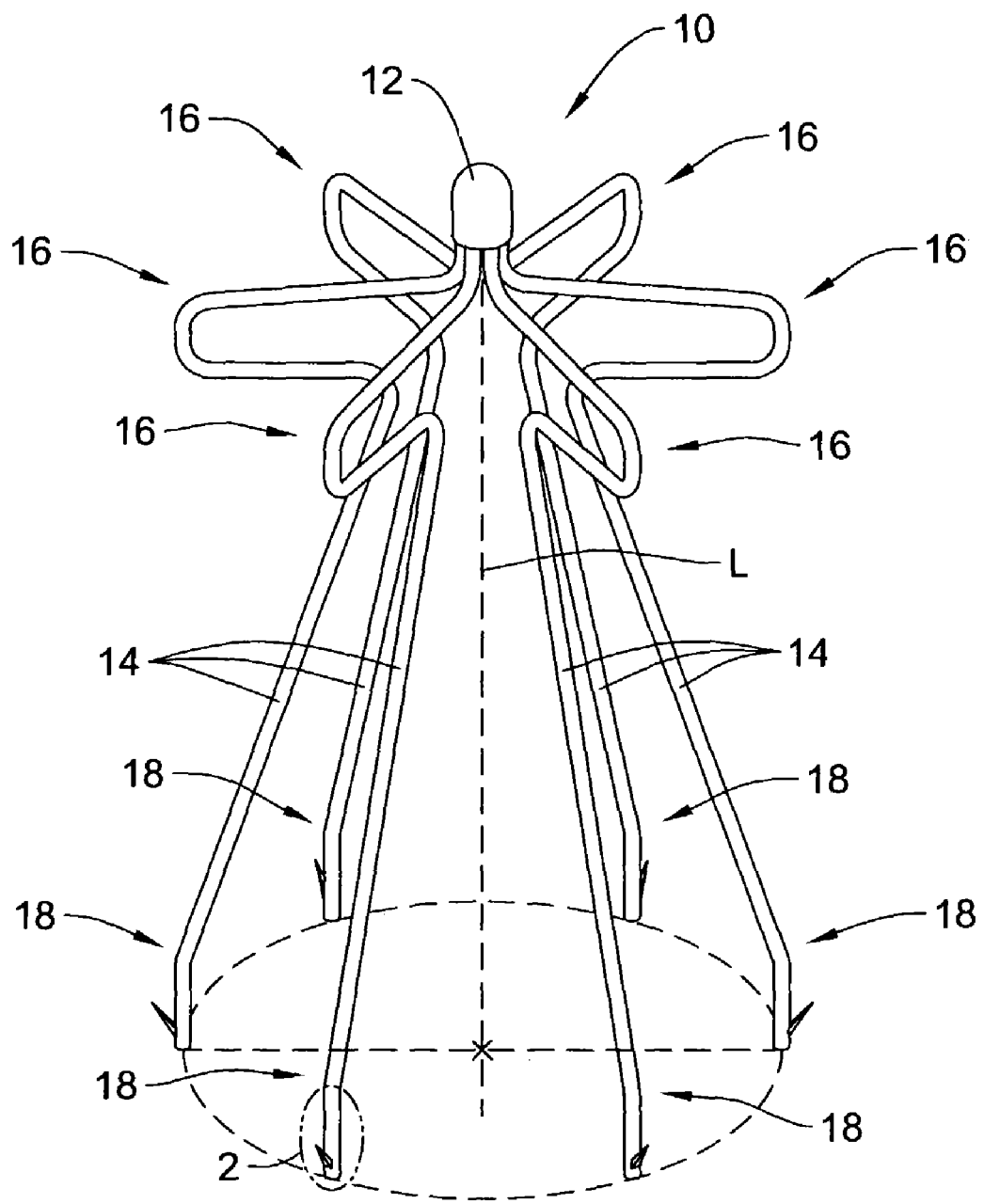
FIG. 1 is a perspective view of a blood clot filter in accordance with an exemplary embodiment of the present invention, showing the filter radially expanded in a centering configuration.

FIG. 1 is a perspective view of a blood clot filter 10 in accordance with an exemplary embodiment of the present invention. Blood clot filter 10 comprises an apical head 12, and a plurality of elongated filter legs 14 each having a proximal section 16 and a distal section 18. As shown in FIG. 1, each filter leg 14 is attached proximally to the apical head 12, forming a common apex of the filter 10. The filter legs 14 are configured to radially expand at the apical head 12, and extend in a diverging manner distally to form a conical-shaped surface. As is discussed in greater detail below, each filter leg 14 may be formed from a shape-memory material configured to revert from a centering configuration having a shape adapted to self-center the filter 10 within the blood vessel to a filtering configuration having a shape adapted to capture blood clots within the blood stream.

The apical head 12 defines a common longitudinal axis L about which the filter legs 14 are configured to radially expand when deployed in the blood vessel. The filter legs 14 can be arranged at equidistant intervals such that the filter legs 14 are radially spaced symmetrically about the longitudinal axis L. In the exemplary embodiment illustrated in FIG. 1, filter 10 includes six filter legs 14 arranged radially at equidistant 60° intervals. The number and arrangement of the filter legs 14 can, of course, vary depending on the particular application. A blood clot filter in accordance with the present invention may include a greater or smaller number of filter legs than illustrated with respect to filter 10, and may be arranged in either a symmetric or asymmetric manner.

In certain embodiments, the filter legs 14 can be formed as separate elements that are then attached to the apical head 12 to form the filter 10. Each filter leg 14 may be formed from an elongated piece of wire having a transverse cross-sectional area that is circular in shape. Other shapes such as rectangular, oval, square, etc. may also be employed. The filter legs 14 can be bonded to the apical head 12 by any number of suitable bonding techniques such as soldering, crimping, welding or adhesion. Examples of suitable welding processes may include laser welding, resistance welding, tungsten inert gas (TIG) welding, plasma welding, electron beam welding, and inertia friction welding. In other embodiments, the filter may be formed from a single workpiece that has been processed to form the apical head 12 and individual filter legs 14. In certain embodiments, for example, filter 10 can be formed from a piece of metallic tubing that has been cut using a laser cutter to form the various components of the filter.

FIG. 2 is an enlarged perspective view of the distal section 18 of one of the filter legs 14 illustrated in FIG. 1. As shown in FIG. 2, the distal section 18 of each filter leg 14 may include an attachment section 20 configured to pierce and secure the filter 10 to the wall of the blood vessel. The attachment section 20 may comprise a hook 22 formed integrally with or coupled to the distal section 18 of the filter leg 14. The hook 22 may be hingedly connected at joint 24 to permit the hook 22 to bend and assume a low profile when the filter 10 is loaded into the delivery device. Each hook 22 may taper distally to a pointed tip portion 26 which, when engaged in the vessel wall, forms a small pin point lesion in the endothelium layer of the blood vessel. The pointed tip portion 26 may be oriented in the proximal direction to resist migration of the filter 10 proximally within the vessel. Although a hook 22 is specifically illustrated in the exemplary embodiment of FIG. 2, it should be understood that attachment section 20 may employ other means for piercing and securing the filter 10 to the vessel wall. For example, a needle, barb, prong, wedge or other suitable attachment means can be utilized in lieu of, or in addition to, the hook 22 illustrated in FIG. 2.

FIG. 3 is a side perspective view of one of the filter legs 14 illustrated in FIG. 1, showing the filter 10 in a centering configuration. As can be seen in FIG. 3, the proximal section 16 of each filter leg 14 may include a bend region 26 that protrudes outwardly away from the longitudinal axis L of the filter 10 towards the vessel wall. At the outermost portion 28 of the bend region 26, the filter leg 14 bends in a direction substantially parallel to the wall of the blood vessel, forming pad that abuts the vessel wall when expanded within the vessel. In use, the bend region 26 centers the apical head 12 within the blood vessel by providing a second point of contact spaced longitudinally apart from the attachment section 20 located on the distal section 18 of each filter leg 14.

The shape of the bend region 26 may be configured to reduce trauma to the vessel wall. For example, as shown in the exemplary embodiment of FIG. 3, the points 30,32 where bend region 26 bends to form the outermost portion 28 may be rounded to reduce any sharp corners that could pierce or distend the vessel. A coating or layer of HYDROPASS or other suitable lubricous material may be placed on all or portions of the filter 10, including bend region 26, to reduce trauma to the body during delivery and deployment. The filter legs 14 may also include an anti-thrombogenic coating such as herapin (or its derivatives), urokinase, or PPack (dextrophenylalanine proline arginine chloromethylketone) to prevent insertion site thrombosis from occurring. An anti-inflammatory agent such as dexamethasone, prednisolone, corticosterone, budesonide, estrogen, sulfasalazine, mesalamine, or any suitable combination or mixture thereof may also be applied to each filter leg 14 to prevent inflammation caused by the engagement of the filter 10 along the vessel wall.

The dimensions of the bend region 26 can be selected to permit the filter 10 to be centered in vessels of different size or shape. In the embodiment illustrated in FIGS. 1-3, for example, the profile of the filter 10 at the bend region 26 is approximately equal to the profile of the filter 10 at the attachment section 22, facilitating centering of the filter 10 in blood vessels having a relatively uniform diameter. In other embodiments, the profile of the filter 10 at the bend region 26 may be greater or less than the profile at the attachment section 22 to facilitate centering of the filter in blood vessels that taper and/or have a tortuous shape.

In another aspect of the present invention, the filter legs 14 may be formed from a shape-memory material that has been heat treated to impart a shape memory effect to filter legs 14, allowing the filter to be transformed from a centering configuration to a filtering configuration within the body. In certain embodiments, for example, the filter legs 14 may be formed of or include a shape memory alloy such as a nickel-titanium alloy (Nitinol) configured to transform from a martensite state at a temperature of about 25° C. to a final austenite transition temperature $A_f$ at about 37° (e.g. body temperature). A cooling fluid such as chilled saline solution may be injected into the lumen of the delivery device to ensure that the filter does not transform to the austenite state prematurely within the delivery device.

In some embodiments, the final austenite transition temperature $A_f$ may be set at a temperature slightly below body temperature to ensure final transition to the filtering configuration at body temperature. As the filter leg 14 is exposed to body temperature when inserted in a blood vessel, the shape-memory material undergoes a transition from martensite to austenite, causing a transformation of the filter leg 14 from the centering configuration to the filtering configuration.

In yet other embodiments, the filter legs 14 may be formed of or include a shape-memory alloy configured to transition from martensite to austenite at temperatures above body temperature. This feature allows the filter 10 to be navigated through the body in a martensitic state, transitioning to the austenite state only upon the application of additional heat using an external heating source. Such methods may include the injection of heated fluid through the delivery device, the use of electrical, microwave or other energy to heat the filter legs 14, or other suitable techniques. In some embodiments, the shape-memory alloy may have a final austenite transition temperature Af in the range of about 37° C. to about 45° C.

The filter legs 14 can be formed of or include any number of suitable shape-memory materials. Examples of suitable shape-memory materials include, but are not limited to, silver-cadmium (Ag—Cd), gold-cadmium (Au—Cd), gold-copper-zinc (Cu—Au—Zn), copper-aluminum-nickel (Cu—Zn—Al), copper-gold-zinc (Cu—Au—Zn), copper-zinc (Cu—Zn), copper-zinc-aluminum (Cu—Zn—Al), copper-zinc-tin (Cu—Zn—Sn), copper-zinc-silicon (Cu—Zn—Si), iron-beryllium ($Fe_3Be$), iron-nickel-titanium-cobalt (Fe—Ni—Ti—Co), iron-platinum ($Fe_3Pt$), indium-thallium (In—Tl), iron-manganese (Fe—Mn), nickel-titanium (Ni—Ti), nickel-titanium-cobalt (Ni—Ti—Co), and/or copper-tin (Cu—Sn). In addition to possessing certain shape-memory properties, the filter legs 14 may have superelastic characteristics that allow the filter legs 14 to bend or flex significantly when loaded into the delivery device without imparting a residual strain.

FIG. 4 is a side perspective view of the filter leg 14 illustrated in FIG. 3, showing the filter leg 14 in a filtering configuration subsequent to heating the shape-memory material beyond its final austenite temperature $A_f$. In the exemplary filtering configuration depicted in FIG. 4, the filter legs 14 are shown assuming a shape similar to that described in U.S. Pat. No. 5,059,205 to El-Nounou et al., the entire contents of which are incorporated herein by reference. Each filter leg 14, for example, may have a slightly outswept shape with one or more U-shaped bends 34 configured to capture blood clots within the blood stream. Although a filtering configuration having U-shaped bends is specifically illustrated in FIG. 4, those of skill in the art should recognize that other shapes may be employed.

Figure 5:
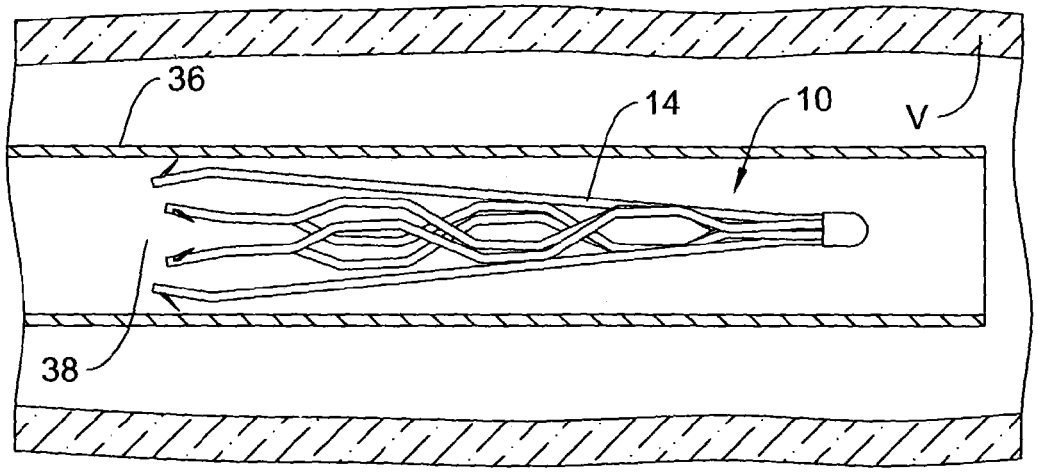
FIG. 5 is a partial cross-sectional view of the blood clot filter of FIG. 1, showing the filter loaded into an introducer sheath and advanced to a target location within a vessel.
Figure 6:
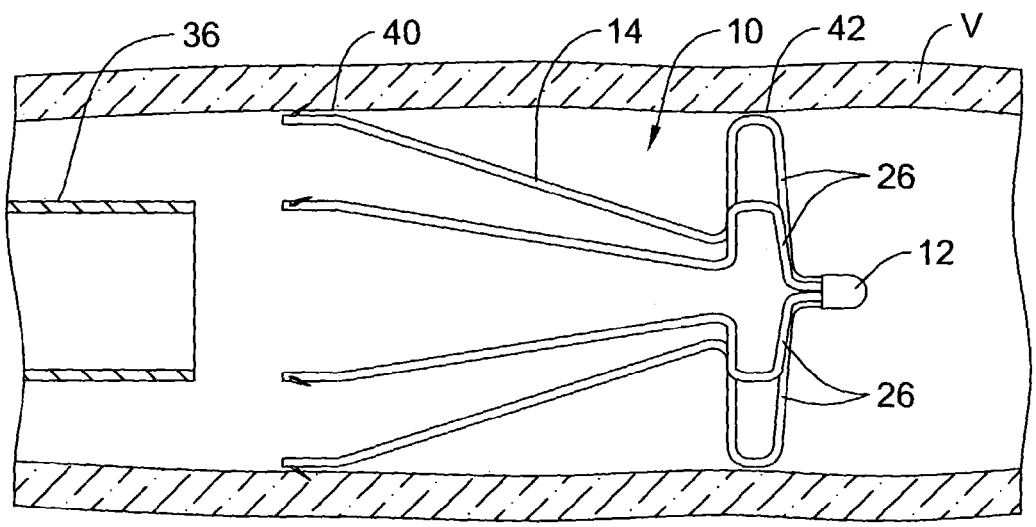
FIG. 6 is another partial cross-sectional view showing the blood clot filter in a centering configuration within the blood vessel.
Figure 7:
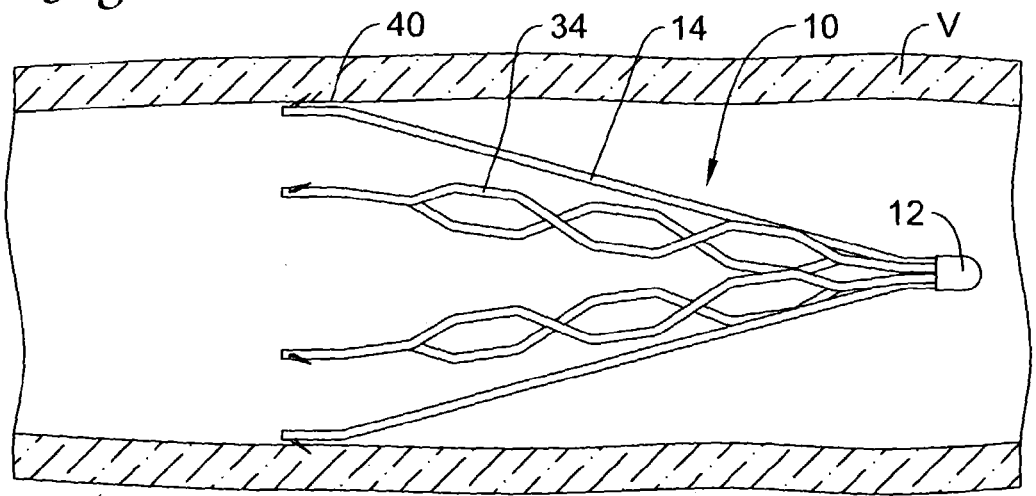
FIG. 7 is another partial cross-sectional view showing the blood clot filter in a filtering configuration within the blood vessel.

Referring now to FIGS. 5-7, an exemplary method of centering a filter in accordance with the present invention will now be described with respect to blood clot filter 10 described above. As shown in FIG. 5, an introducer sheath 36 having an inner lumen 38 may be utilized to transport filter 10 in a radially collapsed position to a desired location within the body such as vessel V. The filter legs 14 may include a binary shape-memory material that has been heat set to revert from a relatively small profile when disposed within the inner lumen 38 of the introducer sheath 36 to a centering configuration when exposed to a heat source, such as body temperature and/or an external heating source.

FIG. 6 is a partial cross-sectional view showing the blood clot filter 10 immediately after removal from within the introducer sheath 36. As illustrated in FIG. 6, as filter 10 is withdrawn from the introducer sheath 36, the filter legs 14 are heated to a temperature sufficient to transform the shape-memory material from martensite to austenite, causing the filter legs 14 to revert to a centering configuration. The transformation to austenite may occur as a result body temperature, or from other external heating means such as an electrode or heated saline. A chilled saline solution can be injected through the inner lumen 38 of the introducer sheath 36 and placed into contact with the filter 10 to prevent the filter legs 14 from transforming to the centering configuration prematurely before deployment.

As further shown in FIG. 6, filter 10 abuts the vessel wall at two longitudinally spaced locations 40, 42 to center the apical head 12 within the blood vessel V. In use, the bend region 26 on each filter leg 14 acts to resist tilting as the attachment section 20 engages the vessel wall. The ability of the filter to self-center upon insertion may, in certain circumstances, improve the efficacy of the filter in a wide range of lumen configurations and placement techniques.

After deployment within the body for a short period of time (e.g. 2-3 seconds), the temperature of the filter legs 14 drops slightly, causing the filter to revert to the filtering configuration. As shown in FIG. 7, for example, the filter 10 may revert to a filtering configuration similar to that described in El-Nounou et al., wherein each filter leg 14 assumes an outswept position having one or more U-shaped regions 34 configured to capture blood clots contained within the vessel V.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. A blood clot filter, comprising:
   an apical head defining a central longitudinal axis; and
   a plurality of elongated filter legs each having a proximal section and a distal section, each of said plurality of elongated filter legs formed at least in part of a shape-memory material actuatable between three mutually exclusive configurations: a radially collapsed configuration, a centering configuration, and a filtering configuration;
   wherein the centering configuration of said plurality of elongated filter legs includes a bend region in the proximal section forming a pad configured to abut a vessel interior wall to center the filter when placed within a blood vessel;
   wherein each of the bend regions of each of the elongated filter legs extends radially outward from the central longitudinal axis at equidistant intervals;
   wherein the apical head is coupled to the proximal section of each of said plurality of elongated filter legs;
   wherein each filter leg is configured to avoid contact with the vessel wall in the proximal section of the filter leg in the filtering configuration.

2. The blood clot filter of claim 1, further comprising attachment means on the distal section of each filter leg for securing the blood clot filter to the blood vessel.

3. The blood clot filter of claim 2, wherein said attachment means comprises a hook.

4. The blood clot filter of claim 1, wherein said shape-memory material is superelastic.

5. The blood clot filter of claim 4, wherein said shape-memory material comprises a nickel-titanium alloy.

6. The blood clot filter of claim 1, wherein said shape-memory material is selected from the group consisting of silver-cadmium, gold-cadmium, gold-copper-zinc, copper-aluminum-nickel, copper-gold-zinc, copper-zinc, copper-zinc-aluminum, copper-zinc-tin, copper-zinc-silicon, iron-beryllium, iron-nickel-titanium-cobalt, iron-platinum, indium-thallium, iron-manganese, nickel-titanium-cobalt, or copper-tin.

7. The blood clot filter of claim 1, wherein said shape-memory material is configured to transform from martensite to austenite at body temperature.

8. The blood clot filter of claim 1, wherein said shape-memory material is configured to transform from martensite to austenite below body temperature.

9. The blood clot filter of claim 1, wherein said shape-memory material is configured to transform from martensite to austenite above body temperature.

10. The blood clot filter of claim 1, wherein said blood clot filter includes a lubricious coating.

11. The blood clot filter of claim 1, wherein the blood clot filter includes six filter legs, wherein the bend regions of the filter legs are arranged at equidistant 60 degree intervals.

12. A blood clot filter, comprising:
   an apical head defining a central longitudinal axis; and
   a plurality of filter legs each having a proximal section and a distal section, the distal section of said filter legs including attachment means configured to secure the blood clot filter at a first location along the wall of a blood vessel;
   wherein each of said plurality of filter legs is formed at least in part of a shape-memory material actuatable between three mutually exclusive configurations: a radially collapsed configuration, a centering configuration, and a filtering configuration;

wherein the centering configuration of each filter leg includes a bend region in the proximal section forming a pad configured to abut the wall of the blood vessel at a second location spaced longitudinally apart from the first location to center the filter within the blood vessel;

wherein each of the bend regions of each of the filter legs extends radially outward from the central longitudinal axis at equidistant intervals;

wherein each filter leg is configured to avoid contact with the wall of the blood vessel in the proximal section of the filter leg in the filtering configuration.

13. The blood clot filter of claim 12, wherein the blood clot filter includes six filter legs, wherein the bend regions of the filter legs are arranged at equidistant 60 degree intervals.

14. The blood clot filter of claim 12, wherein the apical head is coupled to the proximal section of each of said plurality of filter legs.

* * * * *